United States Patent [19]

Ordidge et al.

[11] Patent Number: 4,531,094
[45] Date of Patent: Jul. 23, 1985

[54] METHODS AND APPARATUS OF OBTAINING NMR SPECTRA

[75] Inventors: Roger J. Ordidge, Nottingham; Robert E. Gordon, Oxford, both of England

[73] Assignee: Oxford Research Systems Limited, Oxford, England

[21] Appl. No.: 464,139

[22] Filed: Feb. 7, 1983

[30] Foreign Application Priority Data

Feb. 9, 1982 [GB] United Kingdom ............... 8203685

[51] Int. Cl.³ ............................................. G01R 33/08
[52] U.S. Cl. ..................................... 324/309; 324/307
[58] Field of Search ......................... 324/300, 307, 309

[56] References Cited

U.S. PATENT DOCUMENTS 4,021,726  5/1977  Garroway ........................... 324/309
4,048,555  9/1977  Rupp ................................... 324/320
4,115,730  9/1978  Mansfield ............................ 324/309

Primary Examiner—Michael J. Tokar
Attorney, Agent, or Firm—Cushman, Darby & Cushman

[57] ABSTRACT

A method of obtaining an NMR spectrum from a sample comprising the steps of: maintaining a static magnetic field along an axis which is homogeneous over at least a small volume constituting part of a sample applying a gradient to said magnetic field which varies in one direction orthogonal to said axis while applying an rf pulse to the sample to saturate all nuclei in the said volume except for a slab lying in a plane normal to the said one direction replacing the said gradient by a second gradient to said magnetic field which varies in a second direction orthogonal to said axis and said one direction while applying an rf pulse to the sample to saturate all nuclei in the said volume except for a slab lying in a plane normal to the said second direction, whereby nuclei in a narrow column extending parallel to the said axis have their spins left undisturbed replacing the second gradient by a third gradient to said static magnetic field which varies in a direction parallel to said axis while applying an rf pulse to the sample to selectively irradiate nuclei in a small region of the said column; and finally removing the third gradient and then reading out the free induction decay signal from the selectively irradiated nuclei in the presence of the static magnetic field alone.

21 Claims, 7 Drawing Figures

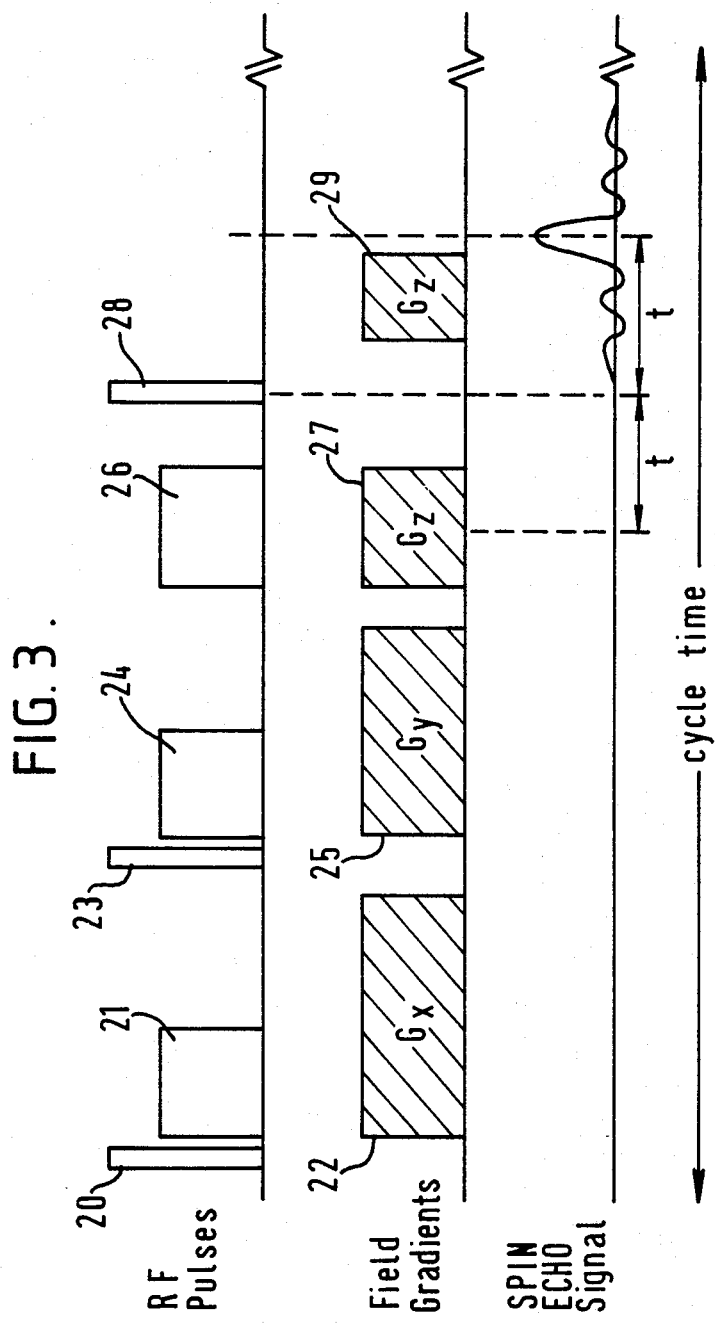

METHODS AND APPARATUS OF OBTAINING NMR SPECTRA

BACKGROUND OF THE INVENTION

This invention relates to a method of obtaining N.M.R. spectra, and to apparatus for use in the said method. In particular, the invention is concerned with obtaining high resolution spectra, and has application where the samples being analysed are inhomogeneous, for example in the examination of living biological tissue.

SUMMARY OF THE INVENTION

According to a first aspect of the invention, there is provided a method of obtaining an N.M.R. spectrum from a sample, which method comprises maintaining along an axis of the sample a magnetic field which is homogeneous over at least a small volume constituting part of the sample, applying to the magnetic field a magnetic field gradient in a first direction, applying to the sample in the presence of the said field gradient an rf pulse to effect the selective saturation of all nuclei of a particular type in the said volume, except for those lying in a slice normal to the said first direction, replacing the field gradient in the first direction by a field gradient in a second direction, orthogonal to the said first direction, and applying to the sample in the presence of the field gradient in the second direction an rf pulse to effect the selective saturation of all nuclei of the said type in the said volume, except for those lying in a slice normal to the said second direction, whereby nuclei in only a narrow column, orthogonal to both the first and second said directions, are unsaturated, replacing the field gradient in the said second direction by a field gradient in a third direction, orthogonal to each of the said first and second directions, applying to the sample in the presence of the field gradient in the third direction an rf pulse to interact selectively with nuclei in the said column and preferably to interact selectively with nuclei in only a short length element of the said column, and thereby obtaining in the substantial absence of applied field gradients, an output signal indicative of the free induction decay of the said selectively affected nuclei in a short length element of the said column.

In a second aspect of the invention, there is provided a method of obtaining an NMR spectrum from a sample comprising the steps of maintaining a static magnetic field along an axis which is homogeneous over at least a small volume constituting part of a sample, applying a gradient to said magnetic field which varies in one direction orthogonal to said axis while applying an rf pulse to the sample to saturate all nuclei in the said volume except for a slab lying in a plane normal to the said one direction, replacing the said gradient by a second gradient to said magnetic field which varies in a second direction orthogonal to said axis and said one direction while applying an rf pulse to the sample to saturate all nuclei in the said volume except for a slab lying in a plane normal to the said second direction, whereby nuclei in narrow column extending parallel to the said axis have their spins left undisturbed, replacing the second gradient by a third gradient to said static magnetic field which varies in a direction parallel to said axis while applying an rf pulse to the sample to selectively irradiate nuclei in a small region of the said column, and finally removing the third gradient and then reading out the free induction decay signal from the selectively irradiated nuclei in the presence of the static magnetic field alone.

In a further aspect of the invention, there is provided apparatus for obtaining an N.M.R. spectrum of a sample, comprising means for applying to a sample a magnetic field which is homogeneous over at least a small volume constituting part of the sample, means for successively applying to the magnetic field magnetic field gradients in each of three mutually orthogonal directions, at least one rf transmitter for applying rf pulses to the sample, and means for controlling the timing and waveform of the output from the said at least one rf transmitter, to apply to the sample selected rf pulses in synchronisation with the said successively applied magnetic field gradients, to selectively interact with nuclei of a particular type in a small element of the said small volume of the sample, and means for obtaining from the said small element an output signal indicative of the free induction decay of the said selectively affected nuclei, and

BRIEF DESCRIPTION OF THE DRAWINGS

The invention will be more readily understood by explanation with reference to the accompanying drawings, in which:

FIG. 3 illustrates in schematic form various alternative waveforms.

DETAILED DESCRIPTION OF THE PREFERRED EMBODIMENT

Figure 1:
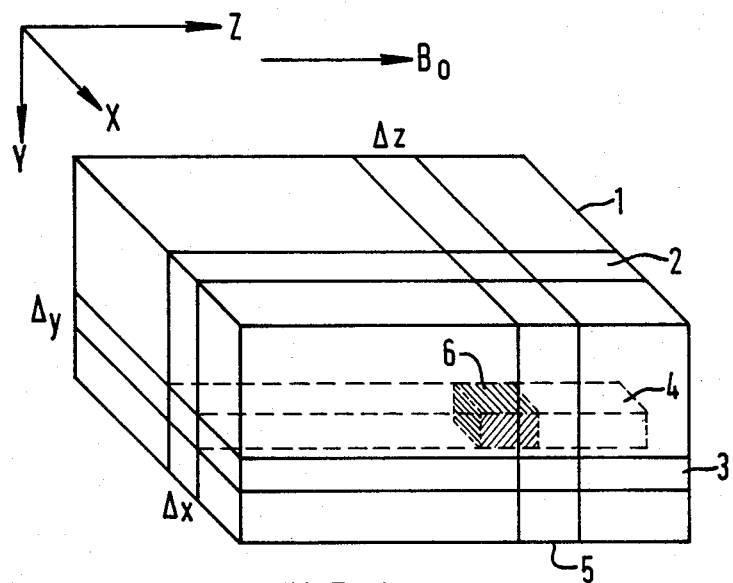
FIG. 1 illustrates in diagrammatic form a sample which it is desired to analyse.

Referring to FIG. 1, a small volume in a sample is represented as a cube 1, positioned with its sides parallel to three orthogonal axes X, Y and Z. Cube 1 is placed in a static homogeneous magnetic field $B_o$, as illustrated in FIG. 1.

In the simplest case, the third direction along which the field gradient is applied is the Z direction (i.e. the direction of $B_o$), and the said first and second directions may, for example be vertical and horizontal directions in the laboratory frame. There is however no necessity that the three directions X, Y and Z should be coincident with any particular direction of the magnet, and for example mutually orthogonal gradients may be produced by the use of combinations of gradient coils as used in a conventional N.M.R. spectrometer. For simplicity however, the invention will be illustrated for the case when the Z direction is coincident with the direction of $B_o$.

A field gradient $G_x$ is applied along the X direction of a sufficient magnitude to provide a measurable difference in rf resonance frequency for nuclei of a particular type in the volume 1. Typical values for the magnitude of the field gradient would be of the order of 0.5 gauss/cm.

Whilst the magnetic field gradient $G_x$ is applied, an rf pulse is applied to the sample so as to effect the selective saturation of nuclei in the sample. The saturation is selective in that all the nuclei of a particular type (typically protons, although any nuclei having a suitable magnetic moment, such as $^{13}C$ or $^{31}p$ could be utilised) within the volume 1 are saturated by the pulse, with the exception of those within a slice $\Delta x$ in the Y,Z plane, i.e. orthogonal to the X axis.

Figure 2:
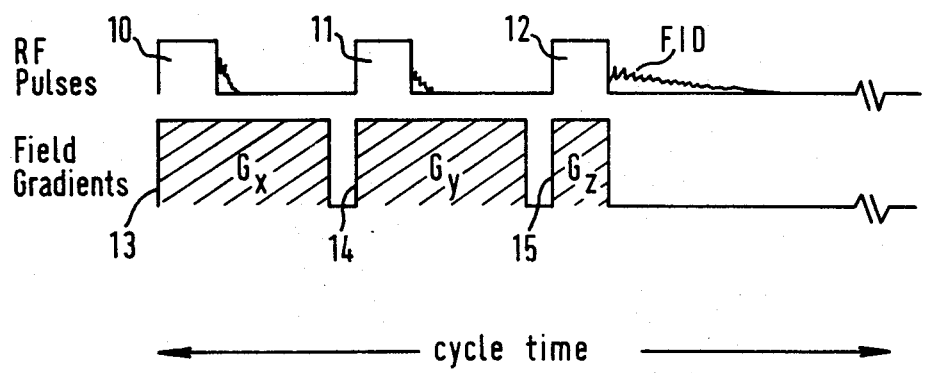
FIG. 2 illustrates in schematic form waveforms to be applied in carrying out a method according to the invention.

FIG. 2 illustrates schematically the time scale over which the rf pulse 10 is applied, in comparison with the field gradient $G_x$.

Figure 4A:
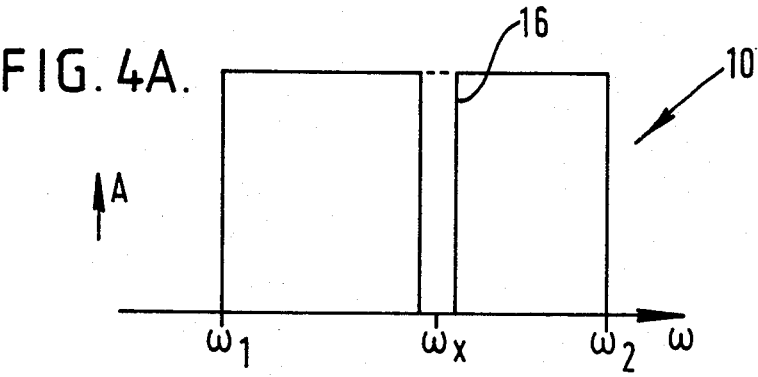
FIGS. 4a–4c are illustrations of desired frequency envelopes for various rf pulses.

To produce the desired saturation of all nuclei *except* those within the slice 2 of thickness $\Delta x$, the radio-frequency pulse applied must have a frequency distribution somewhat of the type illustrated in FIG. 4(a), in which the horizontal axis now represents radiofrequency, and the vertical axis represents amplitude. It can be seen that, in effect, the waveform has a "notch", at a frequency corresponding to the resonant frequency of the slice 2. Such a waveform can be produced by calculating the desired frequency distribution, and applying Fourier transform techniques, to produce the appropriate amplitude modulation for the rf pulse. This technique of pulse shaping is commonly used in nuclear magnetic resonance, and is referred to for example in papers by R. J. Sutherland and J. M. S. Hutchison (J. Phys. E. Sci. Instrum., Vol. 11, 1978), and by J. M. S. Hutchison, R. J. Sutherland, and J. R. Mallard (J. Phys. E. Sci. Instrum., Vol. 11, 1978).

The saturated nuclear spins in the portion of the volume not in the slice 2 are initially in phase, and the gradient $G_x$ is maintained for a period of time sufficient to permit the spins to dephase.

A second field gradient represented by block 14 is FIG. 2 is then applied to the magnetic field in the Y direction. Whilst the magnetic field is applied, an rf pulse 11 is applied to the sample, such as to saturate all the spins of the particular type of nuclei under investigation in the volume, with the exception of those in a slice 3 of thickness. $\Delta y$, in the X,Z plane (i.e. normal to the Y direction). The waveform of the rf pulse 11 may similarly be calculated by Fourier transform techniques.

The net effect of the two pulses 10 and 11 is thus to leave unsaturated only the nuclear spins in a column 4, which is common to both slice 2 and slice 3. This column 4 extends in the Z direction.

A field gradient $G_z$ is now applied in the Z direction, as illustrated in FIG. 2, and an rf pulse 12 is applied to selectively interact with nuclei in a short length of the column 4. The pulse 12 does not interact with those nuclei lying outside column 4, since the spins of those nuclei are already saturated by pulses 10 and 11. Pulse 12 is selected to have a frequency distribution so that it interacts only with those nuclei lying within a slice 5 orthogonal to the Z axis. Thus, only those nuclei lying in a small element 6 of column 4, where column 4 and slice 5 coincide, interact with pulse 12.

The field gradient Z is then removed, and the spins in element 6 are allowed to decay in the absence of any magnetic field gradients, that is to say in the homogeneous static magnetic field $B_o$.

The resulting free induction decay (FID) signal will thus represent almost entirely the transient response from the element 6, and not from any other part from the volume represented by the block 1. The free induction decay signal can be subjected to Fourier transformation in conventional manner, to yield spectral information about the element 6. The cycle represented by FIG. 2 is repeated a sufficient number of times to obtain information of the desired accuracy about element 6, and is then repeated with a pulse waveform 12 having a notional "shape" (represented by FIG. 4(a)) corresponding to a different position along the Z axis for the slice 5. Thus, the length of the column 4 is "scanned", and data obtained for each of the series of element 6 along column 4. In a similar way, the X and Y directions can be scanned, to build up a three-dimensional spectrum for the whole of the volume represented by the block 1.

Figure 4B:
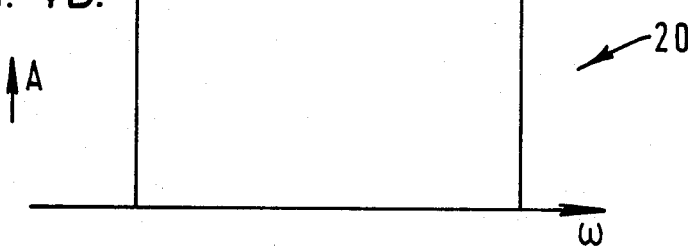

Although the cycle illustrated in FIG. 2 is relatively simple from a conceptual point of view, the tailoring of pulse waveforms to produce a frequency distrubution as shown in FIG. 4(a) is in practice quite difficult to achieve. This is because the amplitude envelope produced by Fourier transformation of the frequency distribution of FIG. 4(a) consists of a fairly sharp pulse of large amplitude, with a number of side pulses of much lower amplitude. Thus, in order to reproduce the waveform accurately, a radio-frequency transmitter with a very large dynamic range is required. Therefore, in a preferred method according to the invention, the selective saturation is achieved using two rf pulses. A first rf pulse saturates substantially all of the nuclei of the appropriate type in the block 1. This pulse can be of relatively short duration (for example from 1 to 500 microseconds, typically 50 microseconds), and high amplitude. The saturation is made selective by a restoring pulse, which is adapted to reverse in the region of the respective slice 2 or 3 the effect of the saturating pulse. This is illustrated schematically in FIG. 3, and the frequency distribution envelopes of the pulses 20 and 21 in FIG. 3 are illustrated schematically in FIGS. 4(b) and 4(c).

By the use of two separate pulses, it is possible either to use two separate radio-frequency transmitters, one adapted for high amplitude and one for low amplitude modulation, or alternatively a single radio-frequency transmitter able to operate in a high amplitude mode, or a low amplitude mode. Thus, significantly better control over the frequency envelope can be obtained. The saturating pulses 20 and 23 will typically have a duration of approximately 50 microseconds, and may be applied either before the application of the respective gradients 22 and 25, or in the presence of these gradients. The presence of gradients during the saturation pulses 20 and 23 will however have the effect of broadening the frequency spectrum over which excitation is required, and thus it is preferred that the saturating pulses 20 and 23 are applied in the absence of field gradients.

Figure 4C:
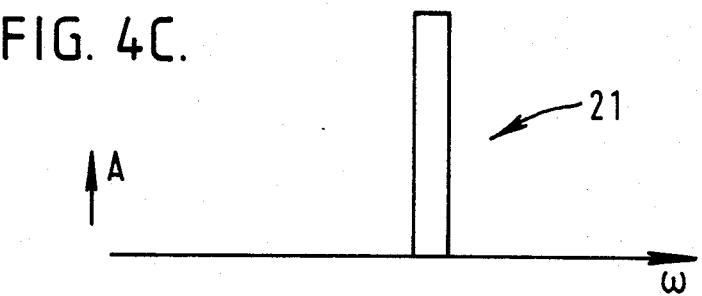

Restoring pulses 21 and 24 may be thought of as representing a frequency distrubution somewhat as shown in FIG. 4(c) and, will be 180° out of phase with the saturating pulses 20 and 23. Restoring pulses 20 and 21 will typically have a duration of from 1 to 5 milliseconds, for example 2 milliseconds.

After application of the pulses 21 and 24, gradients $G_x$ and $G_y$ are maintained for a period of time sufficient to allow dephasing of the saturated spins in the volume block 1. The length of time required will be of the same order as the duration of the pulses 21 and 24, for example 2 milliseconds.

FIG. 3 also illustrates a further preferred technique in accordance with the method of the invention, that of "refocussing" the signal evolution to produce a spin-echo. The refocussing technique is well-known in nuclear magnetic resonance, and is described, for example, in the Sutherland and Hutchison papers mentioned above.

Refocussing can be achieved by applying to the sample after the pulse 26 which is applied in the presence of a gradient 27 in the Z direction, a further pulse 28, such as to cause 180° nutation of the nuclear spins under investigation. In addition, a gradient 29 in the Z direction is applied following the refocussing rf pulse 28. Not only does this method have the effect of producing a spin-echo, but also it has the advantage of removing signal evolution due to magnetic field inhomogeneity, and rephasing the signal evolution from nuclei with different chemical shifts. The free induction decay following will therefore appear to commence from a zero time origin, as illustrated in the lower part of FIG. 3.

The techniques of refocussing are adequately described elsewhere, and such references should be considered to be incorporated herein by reference. It should be noted that the pulse 26 should be tailored so as to enable refocussing of the signal evolution to produce a spin-echo.

An alternative method of refocussing signal evolution is to reverse the direction of the magnetic field gradient $G_z$, after a predetermined period of time.

To produce the desired waveforms, a digital-to-analogue converter may be provided to produce the radio-frequency waveforms, and because of the complexity of the radio-frequency pulses required, it should be noted that a particularly large memory requirement is imposed in respect of the electronics responsible for driving the radio-frequency transmitter.

The strengths or slopes of the gradients to magnetic field B should be strong in comparison with any residual gradients from inhomogenieties in field B. Some of the criteria for determining the strength of the gradients are discussed below.

In a high resolution NMR experiment each nucleus resonates at a field of magnitude B' given by $$B' = (1 - \sigma)B \tag{1}$$

where $\sigma$ is the chemical shift. If this experiment is repeated in the presence of a linear field gradient $G_x$ then for one dimension equation (1) has to be modified as follows:

$$B'_i = (1 - \sigma_i)B \pm G_x x_i \tag{2}$$

where for the $i^{th}$ nucleus $B'_i, \sigma_i$ and $x_i$ are the resonant field, chemical shift and spatial location respectively. Equation (2) can be rearranged to give:

$$B'_i/B = 1 - \sigma_i \pm G_x x_i/B \tag{3}$$

The term $G_x x_i/B$ can be considered as a pseudo chemical shift term. The presence of the gradient $G_x$ therefore extends the chemical shift range. Consequently the spectral band width of the transmitter must be increased accordingly if all the spins are to be excited. If however a narrow part of the chemical shift range is excited by selective irradiation then only nuclei in a slice of thickness $\Delta x$ and mean location $x_m$ will resonate. In other words the effect of applying the gradient $G_x$ has been to spatially label the spins. In general the sample will produce a multi-line spectrum with each line resonating at a particular chemical shift $\sigma_i$ within a range $\pm \sigma_o$, where $2\sigma_o$ is the expected total width of the spectrum.

In a homogeneous static magnetic field the spectra that would be obtained from successive slices $\Delta x$ would be identical but in the presence of a linear gradient $G_x$ the resonant frequency now depends not only on $\sigma_i$ but also on $x_i$ so that the relative positions of the spectral lines within each slice $\Delta x$ will be distorted. Furthermore the relative proportions of these lines may also be altered by lines being frequency shifted outside the selective irradiation bandwidth and by lines from adjacent slices being shifted to be inside the irradiation bandwidth.

Additionally in the presence of a field gradient the individual line shapes will inevitably be broadened so that overlap from adjacent slices can be caused not only by frequency shifts but also by line broadening. Both of these effects can be minimised by choosening $G_x$ such that the irradiation frequency depends mainly on the pseudo chemical shift term. If the slice has a width d then $G_x$ must satisfy the condition that $$G_x \geq 2\sigma_o B/d \tag{4}$$

The above condition for the magnitude of gradient $G_x$ applies equally to the gradients $G_y$ and $G_z$.

As indicated above, the rf pulses are rendered selective by tailoring their pulse shape to suit the required spectral distribution function. An alternative method is to modulate the width of a series of rf pulses. This method is however rather wasteful of rf power, since a great deal appears in undesirable sidebands and harmonics. If the cosine transform c(t) of desired spectral distribution frequency function g($\omega$) is used to amplitude the rf carrier then the resulting spectral distribution will be a doublet e($\pm \omega$) about the carrier frequency $\omega_o$. One of this pair may be suppressed by also modulating with the sine transform s(t) a second carrier wave in quadrature phase with the first, then combining the two channels.

The magnet used to generate the magnetic field may be of any conventional form, for example a superconducting or non-superconducting magnet. It is preferred that the magnet is of a sufficient size to accommodate at least a portion of the body of a patient, so that the method and apparatus of the invention can be used to obtain an N.M.R. spectrum from a sample which is a living body. To this end, the apparatus may be provided with a patient support, for example a chair or bed on which the patient may rest. The magnetic field is preferably homogeneous over a length of at least 10 cm, to enable a spectrum to be obtained from, for example, various elements within a cube of side 10 cms.

Figure 5:
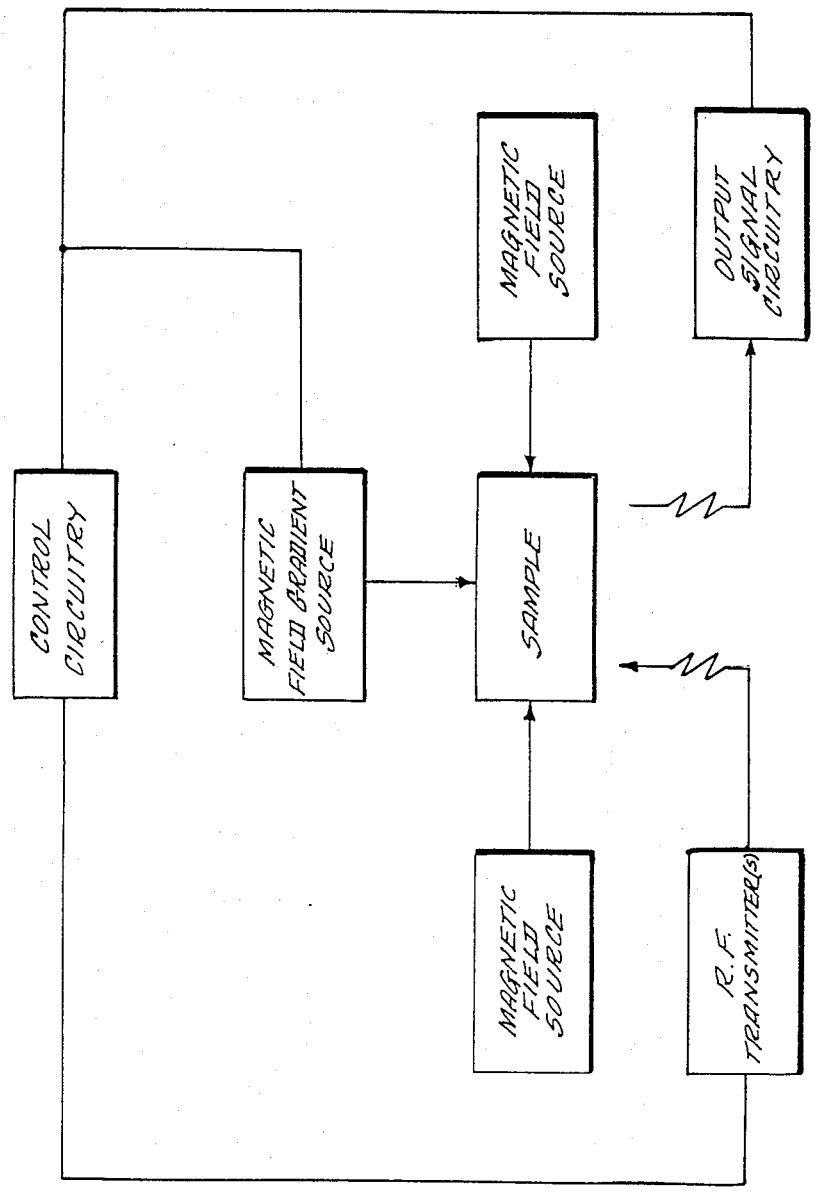
FIG. 5 is a schematic diagram of the apparatus according to the present invention.

FIG. 5 depicts the apparatus according to the invention. Sample 30 is subjected to a magnetic field produced by magnetic field source 31. Magentic field gradient source 32 successively applies magnetic field gradients in each of three mutually orthogonal directions to the sample. Rf transmitter 33 applies selected rf pulses to the sample in synchronization with the applied magnetic field gradients. Output signal circuitry 35 obtains from the sample an output signal indicative of the free induction decay signals in the sample. Control circuitry 34 controls the timing and wave form and synchronizes the rf transmitter 33, the magnetic field gradient source 32, and the output signals circuitry 35.

We claim:
1. A method of obtaining an N.M.R. spectrum from a sample, which method comprises maintaining along an axis of the sample of magnetic field which is homogene- ous over at least a small volume constituting part of the sample, applying to the magnetic field a magnetic field gradient in a first direction, applying to the sample in the presence of the said field gradient an rf pulse to effect the selective saturation of all nuclei of a particular type in the said volume, except for those lying in a slice normal to the said first direction, replacing the field gradient in the first direction by a field gradient in a second direction, orthogonal to the said first direction, and applying to the sample in the presence of the field gradient in the second direction an rf pulse to effect the selective saturation of all nuclei of the said type in the said volume, except for those lying in a slice normal to the said second direction, whereby nuclei in only a narrow column, orthogonal to both the first and second said directions, are unsaturated, replacing the field gradient in the said second direction by a field gradient in a third direction, orthogonal to each of the said first and second directions, applying to the sample in the presence of the field gradient in the third direction an rf pulse to selectively interact with nuclei in the said column, and obtaining, in the substantial absence of applied field gradients, an output signal indicative of the free induction decay of the said selectively affected nuclei.

2. A method as claimed in claim 1, wherein at least one of the rf pulses for effecting the said selective saturation is a restoring pulse, adapted to reverse, in the region of the said respective slice, the saturating effect of a radio frequency pulse adapted to saturate substantially all of the nuclei of the said type in the said volume.

3. A method as claimed in claim 2, wherein the saturating pulse is applied in the substantial absence of field gradients.

4. A method as claimed in claim 3, wherein the saturating pulse has a duration of from 1 to 500 microseconds.

5. A method as claimed in claim 4, wherein the saturating pulse has a duration of about 50 microseconds.

6. A method as claimed in claim 1, wherein the rf pulse applied in the presence of the field gradient in the third direction is such as to enable refocussing of the signal evolution to produce a spin-echo.

7. A method as claimed in claim 6, wherein a further rf pulse is applied to the sample after the rf pulse applied in the presence of the field gradient in the third direction, the said further rf pulse being such as to cause 180° nutation of nuclear spins in the column, whereby to enable refocussing of the signal evolution.

8. A method as claimed in claim 7, wherein a field gradient in the said third direction is applied to the magnetic field after application of the said further rf pulse.

9. A method as claimed in claim 6, wherein refocussing of the signal evolution is carried out by reversing the direction of the magnetic field gradient applied along the said third direction after a predetermined period of time.

10. A method as claimed in claim 1, wherein the gradient in the said first direction is maintained for a period of time sufficient to permit dephasing of nuclear spins of the portion of the said volume not contained within the said slice, before application of the said gradient of said second direction.

11. A method as claimed in claim 2, wherein the magnetic field gradients have a magnitude of about 0.5 gauss/cm.

12. A method as claimed in claim 1, wherein the said third direction is coincident with the said axis of the sample along which the magnetic field is applied.

13. A method of diagnosis carried out on a living body, which method comprises obtaining an N.M.R. spectrum from the body by a method as claimed in claim 1.

14. Apparatus for obtaining an N.M.R. spectrum of a sample, comprising means for applying to a sample a magnetic field which is homogeneous over at least a small volume constituting part of the sample, means for successively applying to the magnetic field magnetic field gradients in each of three mutually orthogonal directions, at least one rf transmitter for applying rf pulses to the sample, and means for controlling the timing and waveform of the output from the said at least one rf transmitter, to apply to the sample selected rf pulses in synchronisation with the said successively applied magnetic field gradients, to selectively interact with nuclei of a particular type in a small element of the said small volume of the sample, and means for obtaining from the said small element an output signal indicative of the free induction decay of the said selectively affected nuclei.

15. Apparatus as claimed in claim 14, including a first rf generator adapted to generate a relatively high amplitude rf signal, and a second rf generator adapted to generate a relatively low amplitude rf signal.

16. Apparatus as claimed in claim 14, including an rf transmitter adapted to be switched between a first mode in which its output is relatively high, and a second mode in which its output is relatively low.

17. Apparatus as claimed in claim 14, including sequencing means for controlling the field gradient applying means and the said at least one rf transmitter, in the following sequence:
  (i) to apply a relatively high magnitude rf pulse in the substantially absence of field gradient, to saturate substantially all nuclei of a particular type in the said small volume,
  (ii) to apply a field gradient in a first direction and a relatively low magnitude rf pulse in the presence of the said field gradient, to selectively desaturate nuclei of the said type lying in a slice normal to the said first direction,
  (iii) to apply a second relatively high magnitude rf pulse in the substantial absence of magnetic field gradient to saturate substantially all nuclei of a particular type in the said small volume,
  (iv) to apply a field gradient in a second of the said three directions, and a relatively low magnitude rf pulse in the presence of the said field gradient to selectively desaturate nuclei of the said type lying in a slice normal to the said second direction,
  (v) to apply a field gradient in the third of the said three directions and a relatively low magnitude rf pulse in the presence of the said field gradient to selectively interact with nuclei of the said type in a small element of the said small volume.

18. Apparatus as claimed in claim 17, whereas the said at least one rf transmitter is sequenced to produce a further rf pulse after step (v), to cause refocussing of the signal obtained.

19. Apparatus as claimed in claim 14, wherein the means for applying a magnetic field to the sample is of a size such as to accommodate within the magnetic field at least a portion of the body of a human patient.

20. Apparatus as claimed in claim 14, incorporating a patient support, for supporting a patient with a portion of the body of the patient in the homogeneous magnetic field.

21. A method of obtaining an NMR spectrum from a sample comprising the steps of maintaining a static magnetic field along an axis which is homogeneous over at least a small volume constituting part of a sample, applying a gradient to said magnetic field which varies in one direction orthogonal to said axis while applying an rf pulse to the sample to saturate all nuclei in the said volume except for a slab lying in a plane normal to the said one direction, replacing the said gradient by a second gradient to said magnetic field which varies in a second direction orthogonal to said axis and said one direction while applying an rf pulse to the sample to saturate all nuclei in the said volume except for a slab lying in a plane normal to the said second direction, whereby nuclei in a narrow column extending parallel to the said axis have their spins left undisturbed, replacing the second gradient by a third gradient to said static magnetic field which varies in a direction parallel to said axis while applying an rf pulse to the sample to selectively irradiate nuclei in a small region of the said column, and finally removing the third gradient and then reading out the free induction decay signal from the selectively irradiated nuclei in the presence of the static magnetic field alone.

* * * * *